(12) United States Patent
Cook

(10) Patent No.: US 10,744,338 B2
(45) Date of Patent: Aug. 18, 2020

(54) BRASSIERE APPARATUS FOR PROPAGATING THERAPEUTIC ELECTROMAGNETIC FIELDS

(71) Applicant: Darin Cook, Oak Harbor, WA (US)

(72) Inventor: Darin Cook, Oak Harbor, WA (US)

(*) Notice: Subject to any disclaimer, the term of this patent is extended or adjusted under 35 U.S.C. 154(b) by 0 days.

(21) Appl. No.: 15/414,976

(22) Filed: Jan. 25, 2017

(65) Prior Publication Data

US 2018/0207438 A1 Jul. 26, 2018

(51) Int. Cl.
*A61N 2/02* (2006.01)
*A61N 2/00* (2006.01)
*H01F 7/06* (2006.01)
*H01F 7/20* (2006.01)
*A41C 3/00* (2006.01)
*A42B 1/24* (2006.01)

(52) U.S. Cl.
CPC ............ *A61N 2/02* (2013.01); *A61N 2/006* (2013.01); *H01F 7/064* (2013.01); *H01F 7/20* (2013.01); *A41C 3/0064* (2013.01); *A42B 1/24* (2013.01)

(58) Field of Classification Search
CPC .......... A61N 2/00; A61N 2/002; A61N 2/004; A61N 2/006; A61N 2/008; A61N 2/02; A41B 2400/32; H01F 7/064
See application file for complete search history.

(56) References Cited

U.S. PATENT DOCUMENTS

| | | | |
|---|---|---|---|
| 2003/0158585 A1* | 8/2003 | Burnett | A61N 1/36021 607/2 |
| 2008/0140155 A1* | 6/2008 | Pilla | A61N 2/02 607/50 |
| 2010/0016651 A1* | 1/2010 | Sivo | A61N 1/40 600/14 |

* cited by examiner

*Primary Examiner* — Carrie R Dorna
(74) *Attorney, Agent, or Firm* — Mohr Intellectual Property Law Solutions, PC

(57) ABSTRACT

A brassiere is configured to administer electromagnetic therapy to treat a cancerous tumor within a breast. The brassiere includes at least one cup, the cup within its walls at least two magnetic coils (also referred to herein as solenoid coils). Each solenoid coil is energized, when in therapeutic operation, with a distinct time-domain signal. The time domain signal consists of a series of summed sinusoidal waves from a power supply. The coils are oriented within the wall of the cup such that for any two coils a first magnetic coil and a second magnetic coil are oriented relative to each other so as to be nonparallel. The purpose of having two distinct coils is to focus resultant magnetic fields such that at a tumor site within a volume of breast tissue the cup encloses to form a local maximum formed by superposition within the cancerous tumor.

15 Claims, 5 Drawing Sheets

US 10,744,338 B2

BRASSIERE APPARATUS FOR PROPAGATING THERAPEUTIC ELECTROMAGNETIC FIELDS

FIELD OF THE INVENTION

The present invention relates generally to brassieres, and in particular to a brassiere wherein cups of the brassier include solenoid coils for focused formation of electric and magnetic fields within the volume of the breast each cup encloses.

BACKGROUND OF THE INVENTION

The American Cancer Society's estimates for breast cancer in the United States for 2016 are:
 About 246,660 new cases of invasive breast cancer will be diagnosed in women.
 About 61,000 new cases of carcinoma in situ (CIS) will be diagnosed (CIS is non-invasive and is the earliest form of breast cancer).
 About 40,450 women will die from breast cancer.

Breast cancer most commonly develops in cells from the lining of milk ducts and the lobules that supply the ducts with milk. Cancers developing from the ducts are known as ductal carcinomas, while those developing from lobules are known as lobular carcinomas. In addition, there are more than 18 other sub-types of breast cancer. Some cancers, such as ductal carcinoma in situ, develop from pre-invasive lesions. The diagnosis of breast cancer is confirmed by taking a biopsy of the concerning lump. Once the diagnosis is made, further tests are done to determine if the cancer has spread beyond the breast and to which treatments it may respond.

Most breast cancers are carcinomas, a type of cancer that starts in the epithelial cells that line organs and tissues like the breast. In fact, breast cancers are often a type of carcinoma called adenocarcinoma, which is carcinoma that starts in glandular tissue. Other types of cancers can occur in the breast, too, such as sarcomas, which start in the cells of muscle, fat, or connective tissue. In any case, however, the cancer, in its early and most treatable stages is a highly-localized structure within the tissue that makes up the breast. For that reason, a highly focused application of any curative regimen is desired; there is no need to treat the surrounding healthy cells. The scope of this embodiment of the instant invention relates to these localized cancerous tumors and not to, for example, inflammatory breast cancer. Because the selected structures for treatment are highly localized, there is no reason to subject the whole of the breast structure where the cancerous cells are contained within a defined volume within the whole of the breast. To the greatest extent possible, the ideal solution would deliver the therapeutic treatment only to affected tissue while leaving the healthy structures alone or minimally involved.

Chemotherapy is the use of drugs to destroy cancer cells, which work by stopping the cancer cells' ability to grow and divide. A chemotherapy regimen (schedule) consists of a specific treatment schedule of drugs given at repeating intervals for a set period of time. Chemotherapy may be given on many different schedules depending on what worked best in clinical trials for that specific type of regimen. It may be given once a week, once every two weeks (also called dose-dense), once every three weeks, or even once every four weeks. Common ways to give chemotherapy include an intravenous (IV) tube into a vein using a needle or in a pill or capsule that is swallowed. As is evident, however, such a treatment involves the whole of the circulatory system and all tissue in contact with the circulating blood receiving chemical agents from the IV tube or the whole of the digestive system and such tissue as receives the chemical agents by means of digestion. As such, a great many healthy structures are dosed with the chemotherapeutic chemical agents which have no need for treatment.

Chemotherapy is predominantly used for cases of breast cancer in stages 2-4, and is particularly beneficial in estrogen receptor-negative (ER-) disease. The chemotherapy medications are administered in combinations, usually for periods of three to six months. One of the most common regimens, known as "AC", combines cyclophosphamide with doxorubicin. Sometimes a taxane drug, such as docetaxel, is added, and the regime is then known as "CAT". Another common treatment is cyclophosphamide, methotrexate, and fluorouracil (or "CMF"). Most chemotherapy medications work by destroying fast-growing or fast-replicating cancer cells, either by causing DNA damage upon replication or by other mechanisms. However, the medications also damage fast-growing normal cells, which may cause serious side effects. Damage to the heart muscle is the most dangerous complication of doxorubicin, for example.

The side effects of chemotherapy depend on the individual, the drug(s) used, and the schedule and dose used. These side effects can include fatigue, risk of infection, nausea and vomiting, hair loss, loss of appetite, and diarrhea. Naturally, these side effects are undesirable and to avoid these side effects while still benefiting from the therapeutic effects the chemotherapy could cause would be highly desirable.

On a molecular level, the listed chemical agents used in chemotherapy cause changes in the molecular structure of cancerous cells. The molecules that make up the chemotherapeutic effectors interact with target biological systems through various physicochemical forces, such as ionic, charge, or dispersion forces or through the cleavage or formation of covalent or charge-induced bonds. These changes effected by physicochemical forces, necessarily assert field effects, i.e. electrostatic and magnetic field effects. Each of the changes involve the movement of charge from one molecular structure to another. Because of these physicochemical-induced movements of charge during interaction, detection of field effects present a record of the chemotherapeutic interactions.

Chemical reactions involve, among other things, the exchange of electrons between valence shell electrons to form or separate compound molecules. Movement of electrons is known as current and that electron movement forms corresponding magnetic fields. Electric and magnetic fields are fundamental in nature and can exist in space far from the charge or current that generates them. Every charged object sets up an electric field in the surrounding space. A changing magnetic field produces an electric field, as the English physicist Michael Faraday discovered in work that forms the basis of electric power generation. Faraday's law of induction describes how a time-varying magnetic field produces an electric field. Conversely, a changing electric field produces a magnetic field, as the Scottish physicist James Clerk Maxwell deduced. Thus, when a first charge moves from a valence shell of an atom, a second charge "feels" the presence of this movement due to the fields produced. The second charge is either attracted toward the initial charge or repelled from it, depending on the signs of the charges. Of course, since the second charge also has an electric field, the first charge feels its presence and is either attracted or repelled by the second charge, too. In short, every chemical reaction causes electrical and magnetic fields to form that are characteristic of that chemical reaction and those fields are detected by other electrons within a given proximity to those fields.

Several have postulated that the chemotherapeutic interactions between a chemical effector and a biological target may not require the presence of the effector itself. Even without the presence of the effector, the object is to induce the same changes in the target by generating field effects associated with effector molecules from signals sensed during action upon targets by effector molecules. By sensing the movement of electrons in successful chemotherapy through recording the generated fields resulting from that movement, the premise asserts that recreating those magnetic and electric fields is sufficient to produce the same therapeutic results without requiring the presence of the chemical effector.

Recognizing that effecting cellular level changes in biological targets by reproducing the suitable electrical and magnetic fields marks the pioneering works of the scientists of Nativis, Inc. as those works are set forth in white papers, patents and patent applications, the instant invention produces highly localized electrical and magnetic field effects. Reducing and eliminating tumors by producing magnetic and electric fields are the gravamen of several studies undertaken to examine the interaction between effector-molecule signals and biological targets. For example, PCT applications WO 2006/073491 A2 and WO 2008/063654 A2, both of which are incorporated by reference herein, teach the application of low-frequency time-domain signals to duplicate field effects the researchers had earlier recorded. These recorded signals comprise low-frequency time domain signals sensed and recorded as emanating from the interaction of one of several bio-active compounds and a biological target such as a matrix of cells (the researchers had isolated these signals observing the application of effectors to induce compound-specific effects in biological target systems). The following is a direct quote from United States Patent Published Application 2011/0195111 entitled "Aqueous Compositions and Methods" and owned by Nativis, Inc.:

PCT application WO 2006/073491, published Jul. 13, 2006 discloses studies in which (a) low-frequency time-domain signals recorded for L(+) arabinose were shown to induce the araC-PBAD bacterial operon, as discussed on pages 47-50 of the application, with respect to FIGS. 30C-30F; (b) low-frequency signals recorded for glyphosphate, the active ingredient in a well-known herbicide, were shown to substantially inhibit stem growth in pea sprouts, as discussed on pages 50-51 of the application, with respect to FIGS. 31 and 32A and 32B; (c) low-frequency signals recorded for gibberelic acid, a plant hormone, were shown to significantly increase average stem length in live sugar pea sprouts, as discussed on pages 51-53 of the application, with respect to FIG. 33; and (d) low-frequency signals recorded for phepropeptin, a proteasome inhibitor, were shown to decrease the activity of the 20S proteosome enzyme, as discussed on pages 53-54 of the application, with respect to FIG. 34.

WO 20081063654 A2, published May 9, 2008, details studies in which low-frequency time-domain signals for the anti-tumor compound paclitaxel, generated in accordance with methods disclosed herein, were shown to be effective in reducing tumor growth in animals injected with glioblastoma cells, when the animals were exposed to an electromagnetic field generated by the signal over a several-week period.

Among the findings from the studies described above is that the ability of agent-specific, time-domain signals to transduce (affect) a biochemical or biological target system can be optimized by a number of strategies. One of these strategies involves scoring recorded time-domain signals by one or more scoring algorithms to identify those signals that contain the highest spectral information. This scoring is used to screen recorded time-domain signals for those that are most likely to give a strong transduction effect. An improvement in this strategy is to record time-domain signals at each of a number of different magnetic-signal injection conditions, by injecting different levels of white noise or DC offset during recording, and scoring the resulting signals for highest spectral information. These strategies are detailed in both of the above-cited PCT applications.

A third strategy, disclosed in the '654 application, is designed particularly for applications in which a recorded time-domain signal is intended for transducing an animal system, for example, for treating a disease condition in a subject. The strategy involves screening time-domain signals for their ability to effectively transduce an in vitro target system that includes at least some of the critical biological response components of the animal system. The strategy has the advantage that a large number of candidate signals can be easily screened for actual transduction effect, to identify optimal transducing signals. The strategy is preferably combined with one or both of the above signal-scoring methods, using the highest-scoring signals as candidates for the in vitro transduction screening.

Independently, a number of scientific groups have reported on the structure and stability of clustered water in pure and solute-containing water samples, including structured water formed at interfaces. See, for example, studies cited in the websites of Dr. Rustum Roy, late of the Pennsylvania State University (rustumroy.com); Dr. Gerald Pollack at the University of Washington (www.depts.washington.eduibioe/people/core/pollack.html)); Dr. Martin Chaplin of the London South Bank University (1.lsbu.ac.uk/wate); and Dr. Emilio Del Guidice (isi.it/progetti/workshop-complexity09/pres_DelGiudice.pdf). Among the findings of these groups is that water interacts with electromagnetic radiation to form stable macroscopic structures that can be detected by a number of physical and spectroscopic tools; (See, for example, del Guidice, E., et al., Physical Review, 74:022105-1 (2006); Pollack, G., uwtv.org/programs/displayevent.aspx?rID=22222): Chai, B. et al, J. Phys. Chem. B, 2009, 113:13953-13958; Rao, M. L., et al., Current Science Research Communications, 98(1); 1500, June 2010.

The application sets out a method of forming an aqueous composition effective to produce an agent-specific effect on an agent-responsive chemical or biological system, when the composition is added to the system. The method includes the steps of:

(a) placing an aqueous medium within the sample region of an electromagnetic-coil device; and (b) exposing the aqueous medium to a magnetic field generated by supplying to the device, a low-frequency, time-domain agent-specific signal, at a signal current calculated to produce a magnetic field strength in the range between 1 G (Gauss) and 10.sup.-8 G, for a period sufficient to render the aqueous medium effective to mimic one or more agent-specific effects on an agent-responsive system.

The low-frequency, time domain signal used in step (b) may be produced by the steps of:

(i) placing in a sample container having both magnetic and electromagnetic shielding, an aqueous sample of the agent, wherein the sample acts as a signal source for low-frequency molecular signals; and wherein the magnetic shielding is external to a cryogenic container;

(ii) recording one or more time-domain signals composed of sample source radiation in the cryogenic container, and (iii) identifying from among the signals recorded in step (ii), a signal effective to mimic the effect of the agent in an agent-responsive system, when the system is exposed to a magnetic field produced by supplying the signal to electromagnetic transducer coil(s) at a signal current calculated to produce a magnetic field strength in the range between 1 G to 10.sup.-8 G.

The inventor of the instant invention makes no assertion as to this science but adopts each of the recited applications in their entirety by the above set-out references. Rather, the inventor, acknowledging the science those references contain seeks, instead, to teach and claim the use of a particularized garment having a plurality of solenoids for the selective propagation of low-frequency, time-domain agent-specific signals throughout selected tissue of a human patient for therapeutic purposes. Nonetheless, the inventor notes that Nativis' flagship therapy and device known together as Voyager is amid clinical trials to "assess the effects of the Nativis Voyager™ therapy in patients with recurrent GBM who have either failed standard of care or are intolerant to therapy. The study will enroll and treat up to 64 subjects of which 32 will be treated with the Voyager therapy alone (monotherapy) and 32 will be treated with Voyager plus concurrent chemotherapy. Safety and clinical utility will be evaluated. See, "A Feasibility Study of the Nativis Voyager™ System in Patients with Recurrent Glioblastoma Multiforme (GBM)" having ClinicalTrials.gov Identifier: NCT02296580.

There is a need for a garment to administer therapeutic electromagnetic fields effectively and discretely to women afflicted by breast cancer. Psychologists recognize a historic aversion among women to be identified as undergoing treatment for breast cancer. The earliest research on the psychological impact of breast cancer focused its attack on femininity, with amputation of the breast, and subsequent threat to sexual attractiveness. In addition to these concerns, the life-threatening nature of cancer itself contributed to psychological distress. The stress of breast cancer has been described as arousing depression, anxiety, and anger. In some of the first systematic and comparative studies, mastectomy patients were found to be more distressed than women with benign lumps, and often this distress persisted for more than a year following surgery. Patients treating for breast cancer report changes in life patterns that resulted from the diagnosis and surgical treatment of breast cancer, including insomnia, recurrent nightmares, loss of appetite, difficulty returning to usual household activities and work, and inability to concentrate.

While noninvasive treatment usually means treatment without surgery, ideally noninvasive treatment of breast cancer means that the treatment also does not invade the life activities of the treated patient. For this reason, it is desired that the treatment of breast cancer is to be as inconspicuous as possible. To avoid the stigma of any clear therapy for breast cancer, what is needed in the art is a means of making the therapy less evident while not in any way diminishing the effectiveness of that therapy. What is needed in the art is a means of facilitating the therapeutic use of solenoids near the targeted tissue of the breast without unwarranted disclosure of the presence of the tumor within the targeted tissue.

SUMMARY OF THE INVENTION

A brassiere is configured to administer electromagnetic therapy to treat a cancerous tumor within a breast. The brassiere includes at least one cup, the cup that includes, in its walls at least two magnetic coils (also referred to herein as solenoid coils). Each solenoid coil is energized, when in therapeutic operation, with a distinct time-domain signal. The time-domain signal consists of a series of summed sinusoidal waves from a power supply. The coils are oriented within the wall of the cup such that for any two coils a first magnetic coil and a second magnetic coil are oriented relative to each other so as to be nonparallel. The purpose of having two distinct coils is to focus resultant magnetic fields such that at a tumor site within a volume of breast tissue the cup encloses to form a local maximum formed by superposition within the cancerous tumor.

The brassiere may, optionally, include a third magnetic coil to receive a third time-domain signal consisting of a third series of summed sinusoidal waves from a third power supply. Just as with the first two magnetic coils, the first magnetic coil and the second magnetic coil, the third magnetic coil is oriented to be perpendicular relative to the others such that each pair of magnetic coils is nonparallel one to the other. The distinct signals that energize the three coils are selected to create by superposition a designated field at the site of the tumor within the volume the therapeutic cup encloses. These signals are defined by a first set of coefficients in the first Fourier series, a second set of coefficients in the second Fourier series, and a third set of coefficients in a third Fourier series and are selected such that a resultant second combined electrical signal formed by superposition forms a local maximum field at the site of a cancerous tumor.

In another embodiment, a fourth magnetic coil is included within the wall of the therapeutic cup to receive a fourth time-domain signal which, likewise, can be defined by a fourth series of summed sinusoidal waves from a fourth power supply. As in the other embodiments, the fourth series of summed sinusoidal waves is also representable as a fourth set of coefficients in a fourth Fourier series. These are selected such that the first magnetic coil, the second magnetic coil, the third magnetic coil, and the fourth magnetic coil are oriented relative to each other such that each pair of magnetic coils is nonparallel one to the other. Also, likewise, the first set of coefficients in the first Fourier series, the second set of coefficients in the second Fourier series, the third set of coefficients in the third Fourier series, and the fourth set of coefficients in the fourth Fourier series being selected such that a resultant third combined electrical signal formed by superposition forms a local maximum at the cancerous tumor.

This embodiment of the brassiere is configured such that each of the first, second, third and fourth magnetic coils are positioned within the brassiere to approximate edges of four respective hulls that together approximate a Reulecaux tetrahedron. A plurality of seams that make up the brassiere cup are used to enclose the magnetic coils.

A method to administer electromagnetic therapy to treat a cancerous tumor within a breast uses a brassiere having at least one therapeutic cup. The cup includes at least a first magnetic coil and a second magnetic coil. Part of the method includes energizing the first magnetic coil with a first time-domain signal which is summed from a first series of sinusoidal waves. Advantageously each series of sinusoidal waves may be represented as a set of coefficients in Fourier series. Likewise, a second magnetic coil is energized by a second time-domain signal consisting of a second series of summed sinusoidal waves. The first magnetic coil and the second magnetic coil are oriented relative to each other so as to be nonparallel, avoiding the structure of a Helmholtz coil, thereby allowing the focusing of the resultant electromagnetic field rather than the uniform field created by a Helmholtz coil. Again, the first set of coefficients in the first Fourier series and the second set of coefficients in second Fourier series are selected such that a resultant first combined electrical signal formed by superposition forms a local maximum at the cancerous tumor.

In another embodiment, the brassiere includes a third magnetic coil which is energized with a third time-domain signal consisting of a third series of summed sinusoidal waves. Just as in the case of the first two signals, the third signal is a series of summed sinusoidal waves also representable as a third set of coefficients in a third Fourier series. The brassiere cup includes the first magnetic coil, the second magnetic coil, and, now, the third magnetic coil which are oriented relative to each other such that each pair of magnetic coils is nonparallel one to the other. The electromagnetic field formed by superposition creates a local maximum at the site of the cancerous tumor. To do so, the first set of coefficients in the first Fourier series, the second set of coefficients in second Fourier series, and the third set of coefficients in the third Fourier series are selected to create a localized field to mimic that of a therapeutic pharmaceutical agent in treatment of a tumor.

A further embodiment of the method includes energizing a fourth magnetic coil the brassiere comprises with a fourth time-domain signal consisting of a fourth series of summed sinusoidal waves. As in the earlier embodiments, the fourth series of summed sinusoidal waves is representable as a fourth set of coefficients in a fourth Fourier series. The coils are oriented about the therapeutic cup such that the first magnetic coil, the second magnetic coil, the third magnetic coil, and the fourth magnetic coil are oriented relative to each other such that each pair of magnetic coils is nonparallel one to the other. The fourth magnetic coil encircles the entrance of the cup. Now, the magnetic field is formed by distinctly energizing each coil with signals. In each coil respectively, the signals include the first set of coefficients in the first Fourier series, the second set of coefficients in the second Fourier series, the third set of coefficients in the third Fourier series, and the fourth set of coefficients in a fourth Fourier series; each Fourier series being selected such that a combined electromagnetic field formed by superposition forms a local maximum at the site of the cancerous tumor.

As described above, the therapeutic cup of the first, second, third and fourth magnetic coils are positioned within the brassiere to approximate edges of four respective hulls that together approximate a Reuleaux tetrahedron. The brassiere cup includes a plurality of seams which are positioned to enclose the magnetic coils in the Reuleaux tetrahedron.

The therapy the invention envisions may be administered using a brassiere assembly to administer electromagnetic therapy to treat a cancerous tumor within a breast. The brassiere assembly includes a brassiere having at least one therapeutic cup, the therapeutic cup including a plurality of solenoid coils, the coils in nonparallel alignment, each to the others. The plurality of solenoid coils are powered by a signal generator, independently energizing each of the plurality of solenoid coils. The signal generator includes a Fourier summing engine to generate summed signals by summing of sinusoids based upon Fourier coefficients provided to the summing engine.

The brassiere assembly is configured such that each of the plurality of solenoid coils receives a distinct signal based upon a distinct series of Fourier coefficients provided to the Fourier summing engine. Each of the distinct series of Fourier coefficients are selected to generate a designated signal at a tumor site within a volume of breast tissue the therapeutic cup encloses, summed from the influence of the plurality of solenoid coils based upon the superposition principle. In the preferred embodiment, the designated signal is selected to mimic electromagnetic fields associated with therapeutic dosage of cancerous tissue with a selected anti-cancer drug.

BRIEF DESCRIPTION OF THE DRAWINGS

Preferred and alternative examples of the present invention are described in detail below with reference to the following drawings.

DETAILED DESCRIPTION OF THE PREFERRED EMBODIMENT

A solenoid is a wire coil wound into a tightly packed helix. When a current of electrons passes along the wire coil, it generates a magnetic field. The term was coined by French physicist André-Marie Ampere to designate a helical coil. Just as electric fields created by different sources, e.g., by two or more point charges, simply add together as vectors, similarly, magnetic fields created by different sources, e.g., by two or more current-carrying wires, also add together as vectors. This is known as the superposition principle and applies to all electric and magnetic fields, including those comprising electromagnetic waves created by different sources. A Helmholtz pair consists of two identical circular magnetic coils (solenoids) that are placed symmetrically along a common axis and when suitably energized, will produce a region of nearly uniform magnetic field.

Figure 1:
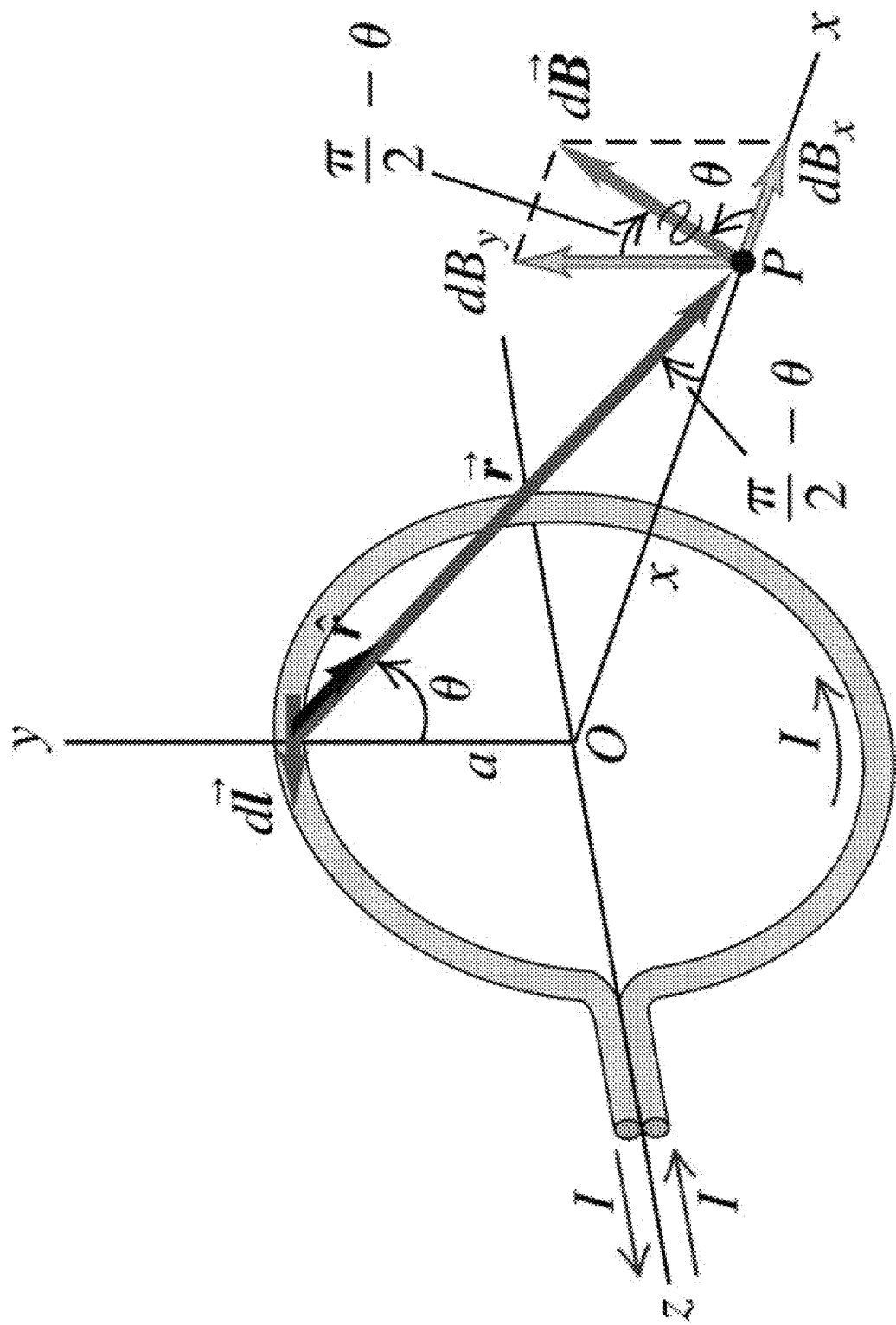
FIG. 1 is a vector diagram depicting a magnetic field strength measured at a point P resulting from a current I passing through a single coil of a solenoid.

Circularity of the coils is not a necessary configuration to form a magnetic field. Consider that, when, rather than a precisely circular or helical coil, the wire coil is allowed to take on a generally triangular shape, the current will still produce a magnetic field which is predicable in its strength and distribution. The Biot-Savart law describes a magnetic field generated by an electric current. The law relates the magnetic field to the magnitude, direction, length, and proximity of the electric current. FIG. 1 shows a circular conductor with radius a that carries a current I. To express the magnetic field at point P on the axis of the loop, at a distance x from the center according to the Biot-Savart Law:

$$\vec{B} = \frac{\mu_0}{4\pi} \int \frac{I}{r^2} d\vec{l} \times \hat{r}$$

A magnetic field decreases with the square of the distance from a "point of current" or current segment. Thus, the Biot-Savart law provides means to calculate the magnetic field created by an electric current flowing through an arbitrarily shaped wire. In fact, the mathematics for calculating magnetic fields produced by irregularly shaped solenoids was used in 1958 to build a stellarator to achieve plasma confinement in a controlled nuclear fusion reaction. Similar calculations can predict, with precision, the number, shape, and position of coils that are required to generate a poloidal magnetic field. Importantly, the field vector indicating the changing magnetic field dB can be resolved into two orthogonal components $dB_x$ and $dB_y$. Thus, when adding magnetic field strength from distinct coils, there is no requirement that the coils be similarly oriented to any arbitrary coordinate system in order to resolve their individual and thus the sum of their individual contributions.

Figure 2:
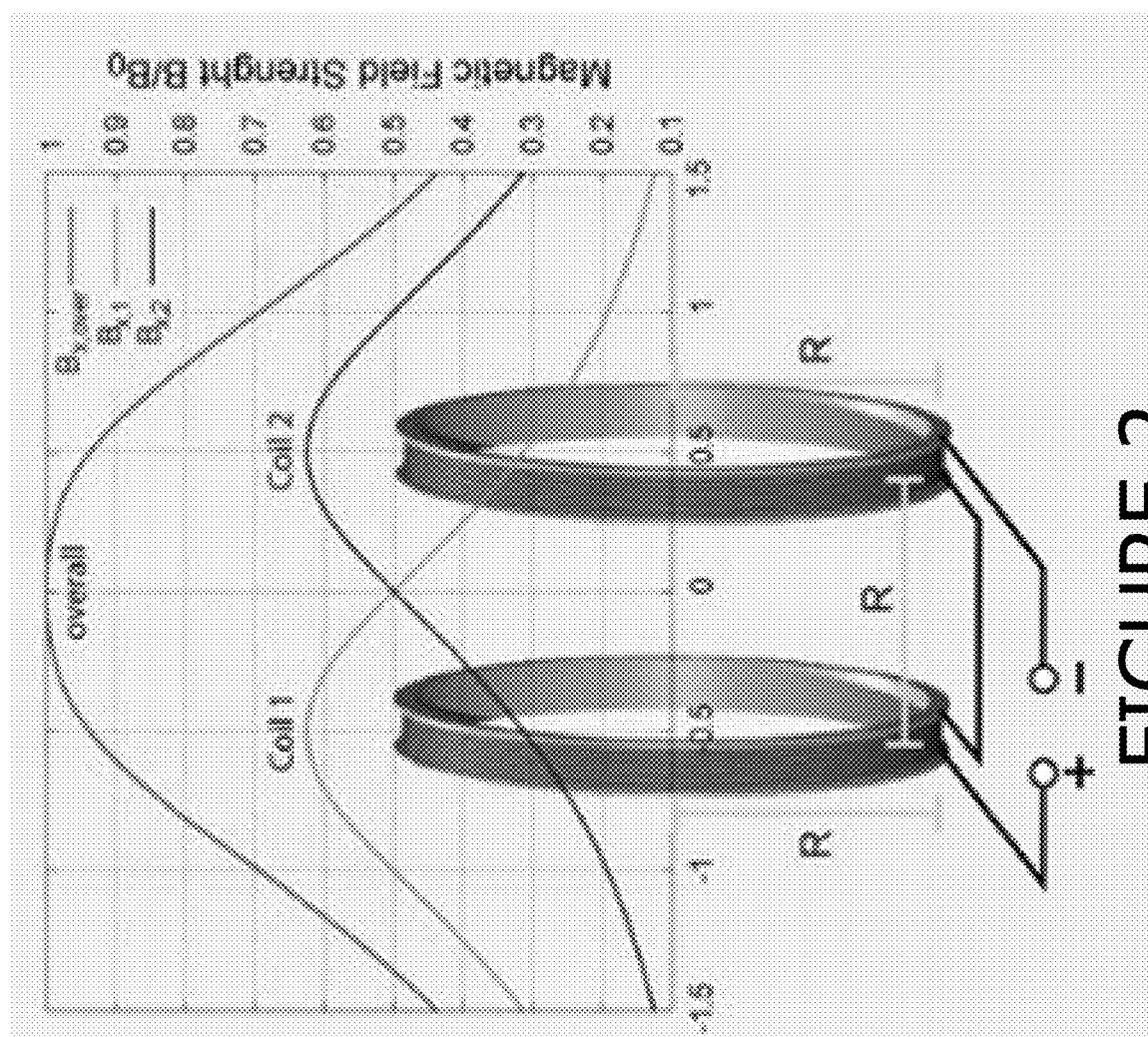
FIG. 2 demonstrates the principle of superposition of magnetic fields based upon individual magnetic fields the two coils of a Helmholtz coil apparatus.

According to the principle of superposition, two (or more) waves can exist in the same spatial location at the same time, and therefore overlap each other. Then one should add up their amplitudes at each spatial location and time moment. FIG. 2 sets out the superposition principle when applied to Heimholtz coils. The Heimholtz coil example set out here is simply to demonstrate superposition but is trivial relative to placement of coils in a bra as the Heimholtz coils are, by definition, perfectly circular and have a radius of R which is also the separation of the coils. Displacement of the coils is solely along the x-axis, so their contribution can be represented in the three graphs shown, i.e. the x-axis component of the magnetic field contributed by Coil 1, the x-axis component of the magnetic field contributed by Coil 2 and Overall (meaning the sum of the x components of the two magnetic fields). While not employed directly in the instant invention, the example of the Heimholtz coils demonstrates the additive nature of magnetic (and, indeed, electric) fields as generated by the current passing around the two coils.

Computational methods have been applied to find resultant fields for currents passing through variously shaped and oriented coils when given each of their relative orientations to develop a desired field at the biological target. That process is facilitated by a correlation between the shape factors and corresponding Fourier coefficients, called the spectrum. When using the proper Fourier coefficients in an expansion, one can produce the desired magnetic field strength in terms of desired angles. These coils should be smooth so they can be constructed effectively and so they generate a magnetic field with robust flux surfaces devoid of extraneous harmonics. If the Fourier coefficients that occur are chosen carefully, the Biot-Savart separatrix thus obtained becomes a good enough facsimile of the fields observed in the corresponding chemotherapeutic reaction to produce the therapeutic result. Thus, by knowing the shape and location of the biological target within a space tinder the influence of a multiplicity of coils, one can selectively energize each of the multiplicity of coils to produce a highly-localized field that replicates the field produced by chemical reactants upon the tumor. According to the earlier work referred to and incorporated above, the effect should be to reduce the tumor.

In the instant invention, the solenoids are positioned as windings running along seams of bra cups. Because bra cups are designed to enclose and support the breast tissue, they provide a pair of relatively stable platforms upon which to fix the therapeutic coils relative to the breast tissue and, therefore, relative to the biological target or tumor. When worn, the brassier or bra maintains a relatively fixed relationship to the structure of the breast. A bra surrounds the breast contacting the surface of the breast with seams that run, generally from the chest wall of a wearer to the tips of the nipples. As such, seams of a brassier or bra can provide hiding places that can be used for positioning solenoids relative to the position of the breast, thereby to focus magnetic and electric fields at a tumor site within the breast. Advantageously, the shape and configuration of the bra is known to be acceptable to women and a woman's election to wear a bra is not significant of any health condition. Suitably hidden, then, the solenoid coils do not advertise the presence or treatment of a tumor.

Figure 3:
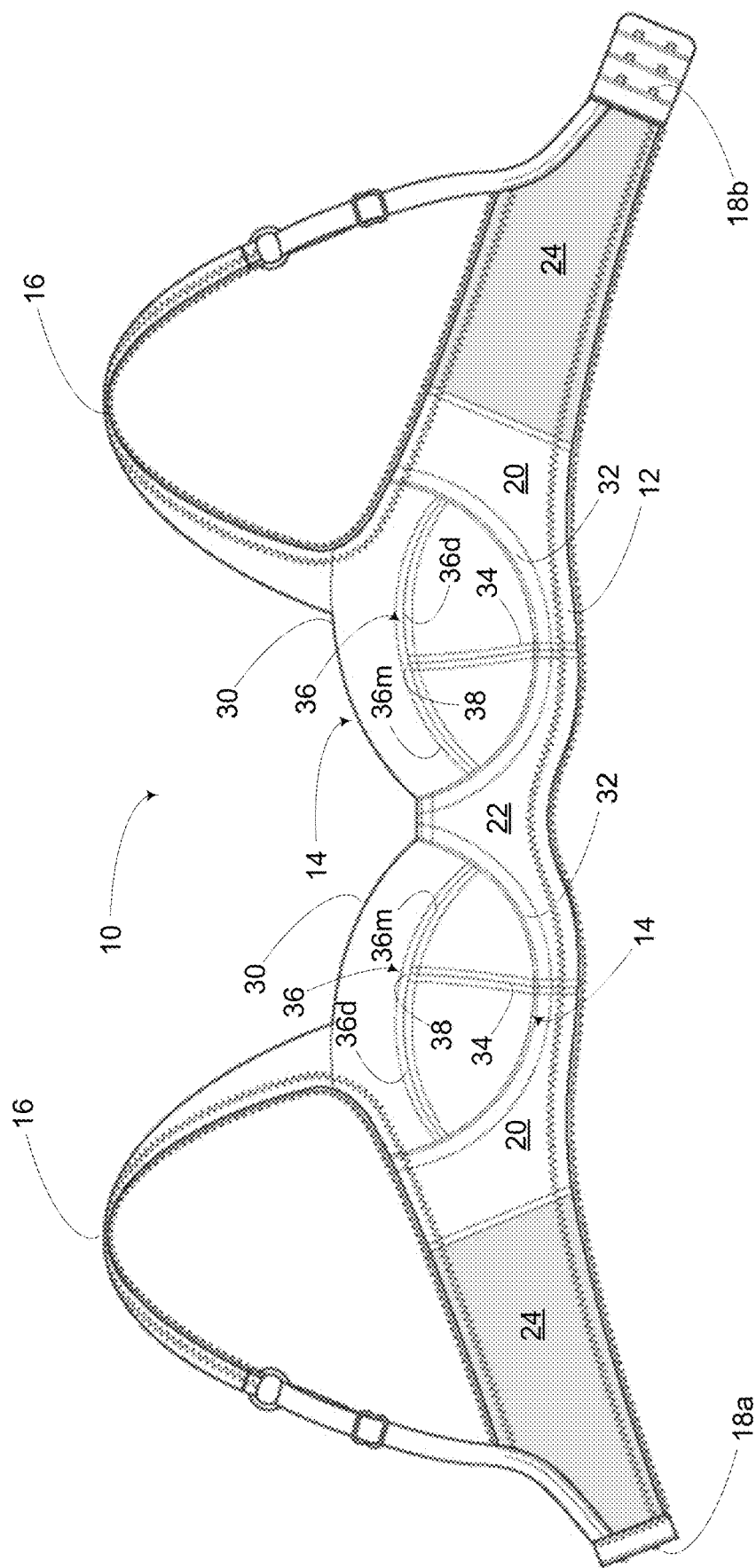
FIG. 3 is a diagram of a conventional brassiere indicating the location of specific seams to conceal solenoid coils.

Because its structure has become conventional, there are components in common with most bras and the known structure provides a lexicon for description. A common configuration for a bra 10 is shown in FIG. 3. A chest band 12 wraps around the torso of the wearer and that chest band 12 provides the mechanical connection to each of two cups 14 for containing and supporting the breasts and shoulder straps 16 which fix the position of the bra 19 relative to the shoulders of the wearer. The chest band 12 is usually closed in the back by a hook 18a and eye 18b fastener, but may be fastened at the front. The chest band 12 and cups 14, not the shoulder straps 16, are designed to support the weight of women's breasts. The section between the cups is called a gore 22. The section under the armpit where the band joins the cups is called the back wing 24. Between the back wing 24 and the cup 14 on each side is a cradle 20 which helps position the cups securely against the chest. Many women therefore find bras with cradles more comfortable to wear.

Importantly, there remains the denotation of seams. To shape planar swatches of cloth around a breast, several seams are necessary to join the swatches and, thereby, to create a hollow to encompass the breast. The breast has a very complicated geometry. Morphologically the breast is a cone, with the base at the chest wall and the apex at the nipple, the center of the nipple-areola complex. Due to both effects of gravity and the nature of the breast tissue, the superior pole of the breast is generally shaped as a half a cone while the inferior pole resembles a half a globe. As with any polyhedron the more faces the swatches provide, the closer the cup will approach the actual shape of the breast.

Shown in FIG. 3 are four distinct and exemplary seams. A seam that joins the cradle to the cup is cup to cradle seam 32. This cup to cradle seam 32 is significant because it often, in a conventional bra, makes up an underwire casing. An underwire bra (also under wire bra, under-wire bra, or underwired bra) is a brassiere that utilizes a thin, semicircular strip of rigid material fitted inside the brassiere fabric. The wire may be made of metal, plastic, or resin. It is sewn into the bra fabric and extends along the underside of each cup 14, extending from the center gore 22 to a spot on the cradle under the wearer's armpit. The wire helps to lift, separate, shape, and support a woman's breasts. The underwire casing comprises a sturdy enclosure for the underwires and stabilizes the cup to cradle seam 32. Importantly, then, the placement of coils of wire, such as those that make up solenoids within the cup to cradle seam 32 is not unusual nor would the presence of those wires signal that the wearer was undergoing any form of therapeutic treatment.

Each cup 14 is defined on its uppermost edge with a seam to finish the cup. That seam is referred to herein as the neckline seam 30. Just as are the seams discussed above and below, the neckline seam 30 can be configured to enclose wires of a solenoid to complete a leg of a triangular loop.

The placement of remaining seams as shown in FIG. 3 is merely one single and exemplary configuration of the invention and others are certainly possible and may be particularly advantageous for treatment of a tumor based upon its location. From a fashion point of view, the more seams there are, the greater is the ability for the cup 14 to shape the breasts. Seamed bras often fit better than their contour cup counterparts and in the case of the instant invention, the more closely the cup conforms with the breast, the better the opportunity to focus electromagnetic fields upon tumors within the breast tissue. With a seamed bra, two or more pieces of fabric are selected to conform and accent breast shape. Cosmetically, the seams also act to support the breasts so the tissue can be lifted higher, shaped better and held in a more fixed relation to the seam-enclosed solenoids.

Fashion dictates that seaming across the cup can follow any of several orientations; the three most common orientations found in conventional bras are the diagonal seam, the horizontal seam and the vertical seam. In conventional fashion, all seams in a bra cup must cross the bust point 38, i.e. the fabric that immediately covers the nipple, or very close to it. By enclosing the solenoid in the seam, each solenoid extends from where the breast tissue contacts the chest wall to the nipple and this same orientation of seams, within a brassiere, allows orientation of solenoids (contained within the seams of a bra) to exploit the principle of superposition thereby to focus fields at a specific location within the volume of the breast as the localized point for therapeutic treatment.

A horizontal bra seam 36 will start and end at the cup to cradle seam 32 extending over the bust point 38 generally within a plane parallel to the horizon. Horizontal cups often incorporate the use of a split lower cup as shown in FIG. 3. Horizontal seams 36 are the seams of choice for strapless bras or for cups that have a straight top edge—the horizontal seam 36 is then placed generally parallel to a top edge of each cup 14, and it creates a very balanced look to the cup 14. Cosmetically it is also the best seaming choice for very large cups.

Another possible configuration not shown in FIG. 3 is that comprising a diagonal seam. Distinct from the horizontal seam 36, the diagonal seam has its origination somewhere in the armhole curve of the cup 14, anywhere between a strap 16 attachment point and the cup to cradle seam 32. Like a horizontal seam, the diagonal seam can be tilted higher or lower within its limited space, depending on the look or therapeutic coverage that is desired. A high diagonal seam many feel is a more flattering seamline for the wearer. It, too, can also be paired with a split lower cup, although the split is often tilted more toward the side seam, so as to form more of a "T" seam at the cross cup.

Still another possible configuration includes a vertical seamline starting anywhere along the top edge of the cup 14, between the strap attachment 16 point and the cup to cradle seam 32 in or near the gore 22. A vertical seam starts anywhere along this edge.

As shown in FIG. 3, a vertical seam 34 transects the horizontal seam 36 at the bust point 38 to define two seam segments: a medial horizontal seam 36m and a distal horizontal seam 36d. If one considers the encompassed breast as bounded by these three seam segments, the vertical seam 34, the medial horizontal seam 36m and the distal horizontal seam 36d, the volume available for treatment would approximate a Reuleaux tetrahedron.

Figure 4:
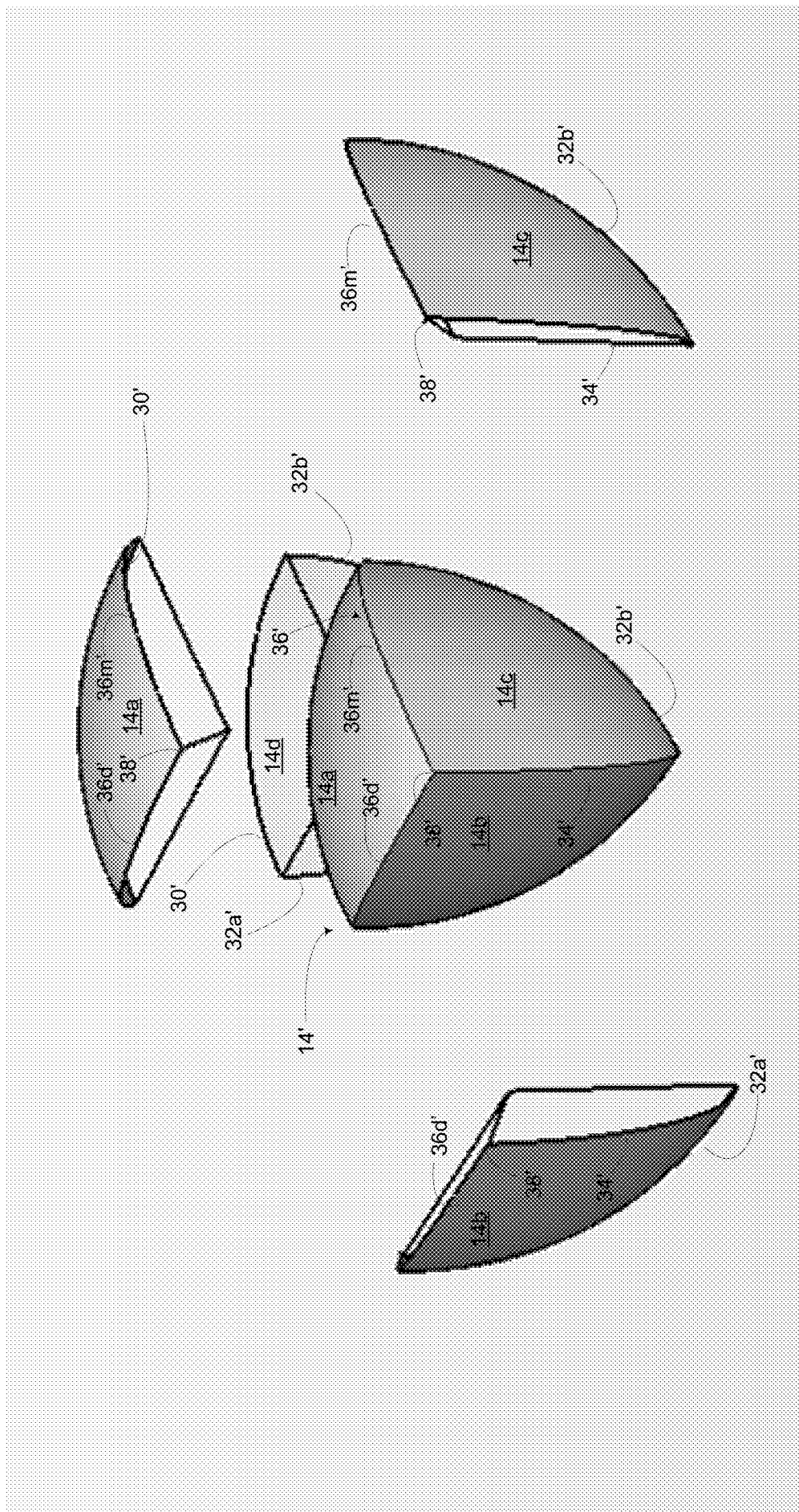
FIG. 4 represents a mapping of the bra cup onto the Reuleaux tetrahedron and the further explosion of the Reuleaux tetrahedron into the four hulls.
Figure 5:
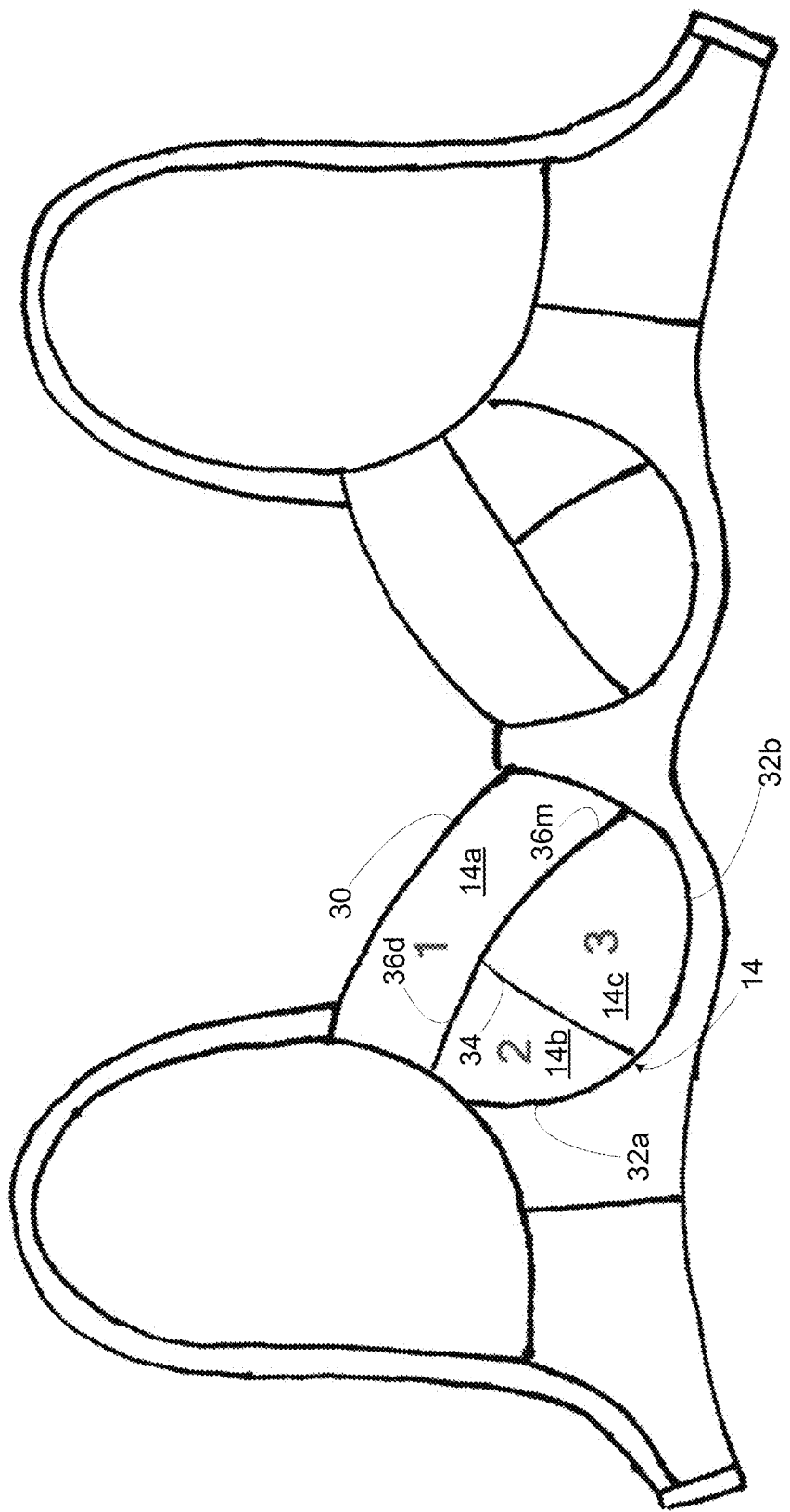
FIG. 5 depicts the selected energization of solenoids concealed within seams of a conventional brassiere.

Referring to FIG. 4, then, the Reuleaux tetrahedron 14' is a mapping of the right cup of the bra shown in FIG. 3 onto an idealized volume of breast tissue. Any Reuleaux tetrahedron is the intersection of four congruent spheres, each having radius s and centered at the vertices of a regular tetrahedron with side length s. The sphere through each vertex passes through the other three vertices, which also form vertices of the Reuleaux tetrahedron. This and every Reuleaux tetrahedron 14' has the same face structure as a regular tetrahedron, but with curved faces: four vertices, and four curved faces, connected by six circular-arc edges. If the vertical seam 34 is mapped onto the Reuleaux tetrahedron 14' we will refer to the vertical seam as 34', the medial horizontal seam 36m is mapped as 36m', the distal horizontal seam 36d is mapped as 36d' and the bust point 38 mapped as 38'. In a similar manner when mapping the idealized breast onto the Reuleax tetrahedron 14' one vertex corresponds to the mapping of the bust point, and, thus, the nipple at 38'. Consistent with the mapping of the right bra cup onto the Reuleaux tetrahedron 14' and we see that the volume of the breast tissue available for treatment is approximated as:

$$\frac{s^3}{12}(3\sqrt{2} - 49\pi + 162\tan^{-1}\sqrt{2}) \approx 0.422s^3$$

It is helpful when visualizing the placement of the solenoids to decompose the Reuleaux tetrahedron into four congruent pieces or hulls 14a-d, each being the convex hull of the centroid and one face (i.e., each piece is the space between the center of mass of Reuleaux or spherical tetrahedron 14' and a given face). The discrete volume of each of the hulls 14a-d is not significant as propagated magnetic fields will influence the whole of the right breast, but the separation into four distinct but congruent hulls 14a-d allows discussion of the edges as distinct triangular solenoids and moves the reader into consideration of four distinct solenoids, each solenoid bordering a face, each face being defined by the seams of the cup.

Each of the four faces are a "Reuleaux spherical triangle," a "circular spherical triangle" obtained by intersecting three circles having equal radius to that of the sphere. Each of circles goes through the centers of the other two. (A spherical triangle is a triangle on the sphere whose sides are arcs of great circles. Thus, a circular spherical triangle is what one gets when circular arcs replace the great circle sides.) In the instant invention, each face is bounded by a three seams which, together, approximate a Reuleaux spherical triangle and faces 14a-c correspond to panels of the right cup of the brassier. The fourth hull, 14d is a mapping of the surface of the chest cavity where it contacts the breast tissue.

FIG. 4 represents a mapping of the bra cup onto the Reuleaux tetrahedron and the further explosion of the Reuleaux tetrahedron into the four hulls 14a-d each having a face that is a Reuleaux spherical triangle bounded by the mapping of seams onto the hulls 14a-d. Each seam can be exploited to discretely house a series of coils for generation of a magnetic field at the site of target tissue.

Considering, then, each of the hulls 14a-d shown in FIG. 4 in order:

Hull 14*a* is bounded by the mapping of the distal horizontal seam 36*d*', the mapping of the medial horizontal seam 36*m*' and the mapping of neckline seam 30'. The bust point is mapped to one vertex 38'. The Releaux spherical triangle that is the face of hull 14*a* would be referred to as an upper cup panel in the parlance of bra manufacture;

Hull 14*b* is bounded by the mapping of the distal horizontal seam 36*d*', the mapping of a segment (extending from cradle 20 at the distal horizontal seam 36*d* to the vertical seam 34) of the cup to cradle seam 32*a*' and the mapping of vertical seam 34'. Again, the bust point is mapped to one vertex 38'. The Releaux spherical triangle that is the face of hull 14*b* would be referred to as a cradle side cup split panel in the parlance of bra manufacture;

Hull 14*c* is bounded by the mapping of the medial horizontal seam 36*m*', the mapping of a segment (extending from gore 22 at the medial horizontal seam 36*m* to the vertical seam 34) of the cup to cradle seam 32*b*', and the mapping of vertical seam 34'. This third hull 14*c* is the last to share the bust point, which is mapped to one vertex 38'. The Releaux spherical triangle that is the face of hull 14*c* would be referred to as a gore side cup split panel in the parlance of bra manufacture;

Hull 14*d* is bounded by the mapping of the neckline seam 30', the mapping of the distal horizontal seam 36*d*', the mapping of the segment (extending from cradle 20 at the distal horizontal seam 36*d* to the vertical seam 34) of the cup to cradle seam 32*a*', and the mapping of the segment (extending from gore 22 at the medial horizontal seam 36*m* to the vertical seam 34) of the cup to cradle seam 32*b*'. The Releaux spherical triangle is not a part of the bra as its boundaries define the rim of the right cup 14 and admit the breast to enclose its volume. There is no corresponding panel of the brassiere.

In use, then, the cup for the breast containing the tumor would receive, in this exemplary embodiment, four distinct low frequency signals; each signal independently energizing the solenoid coils in each of the panels defined by the seams. The independent signals allow the focused application of magnetic and electric field in an closely circumscribed volume that contains the tumor. So, for example the six seams the distal horizontal seam 36*d*, the medial horizontal seam 36*m*, the neckline seam 30; the cup to cradle seam 32*a*, the cup to cradle seam 32*b*, and the vertical seam 34 define the boundaries of the three panels and the opening to the brassiere. The vertical seam 34 joining the distal horizontal seam 36*d* and the medial horizontal seam 36*m* at the bust point 38. Each permutation of the seams defines one region of the brassiere 10, each region being bounded by a distinct solenoid such that, as demonstrated in FIG. 4, four distinct solenoids bound four distinct hulls, three of which are represented by distinct panels in the brassiere (the fourth region is bounded by the cup to cradle seam 32 and the neckline seam 30 but is really behind this projection of the right brassiere cup 14 and not shown herein).

By selectively energizing each solenoid, i.e. 1 (the upper cup), 2 (the distal split cup), 3 (the medial split cup), and 4 (the opening), a control unit can generate each an electric and a magnetic field within the volume of the breast. Advantageously, because the Nativis work is based upon application of specific, low energy, non-invasive, non-thermal and non-ionizing oscillating electromagnetic signals, these four solenoids can reconstruct, as the sum of their individual fields, signals to inhibit in vitro tumor cell proliferation. These reconstructed signals ought to be able to produce a more localized anti-mitotic effect than the single solenoid Nativis relies upon to date. Methods: Conventionally, the Nativis Voyager™ relies upon propagation of a single RFE signal applied using a rectangular 40 mG coil. One can readily surmise that within a system based upon generating a localized field signal like that of the Nativis Voyager™ RFE System only to do so at the precise site of the tumor rather than on that surface of the breast closest to the tumor, tumor growth would be similarly interrupted. Because the fields would reach their maximum strength only at the tumor site, side effects would be minimized. Because the magnetic field of the summation of the contributions from each of the coils, the noncancerous tissue would be minimally affected. In short, the instant invention will be maximally effective in administering focused fields because of the distinct orientations of multiple solenoids.

While the preferred embodiment of the invention has been illustrated and described, as noted above, many changes can be made without departing from the spirit and scope of the invention. Accordingly, the scope of the invention is not limited by the disclosure of the preferred embodiment. Instead, the invention should be determined entirely by reference to the claims that follow.

The embodiments of the invention in which an exclusive property or privilege is claimed are defined as follows:

1. A brassiere to administer electromagnetic therapy to treat a cancerous tumor within a breast, the brassiere comprising:
   a cup, the cup comprising at least:
      a first magnetic coil to receive a first time-domain signal consisting of a first series of summed sinusoidal waves from a first power supply, the first series of summed sinusoidal waves being representable as a first set of coefficients in a first Fourier series; and
      a second magnetic coil to receive a second time-domain signal consisting of a second series of summed sinusoidal waves from a second power supply, the second series of summed sinusoidal waves being representable as a second set of coefficients in a second Fourier series, wherein the first magnetic coil and the second magnetic coil are oriented relative to each other so as to be nonparallel, the first set of coefficients in the first Fourier series and the second set of coefficients in second Fourier series being selected such that a resultant first combined electrical field formed by superposition forms a local maximum at the cancerous tumor.

2. The brassiere of claim 1, further comprising:
   a third magnetic coil to receive a third time-domain signal consisting of a third series of summed sinusoidal waves from a third power supply, the third series of summed sinusoidal waves being representable as a third set of coefficients in a third Fourier series, wherein the first magnetic coil, the second magnetic coil, and the third magnetic coil are oriented relative to each other such that each pair of magnetic coils is nonparallel one to the other, the first set of coefficients in the first Fourier series, the second set of coefficients in second Fourier series, and the third set of coefficients in the third Fourier series being selected such that a resultant second combined electrical field formed by superposition forms a local maximum at the cancerous tumor.

3. The brassiere of claim 2, further comprising:
   a fourth magnetic coil to receive a fourth time-domain signal consisting of a fourth series of summed sinusoidal waves from a fourth power supply, the fourth series of summed sinusoidal waves being representable as a fourth set of coefficients in a fourth Fourier series, wherein the first magnetic coil, the second magnetic coil, the third magnetic coil, and the fourth magnetic coil are oriented relative to each other such that each pair of magnetic coils is nonparallel one to the other, the first set of coefficients in the first Fourier series, the second set of coefficients in the second Fourier series, the third set of coefficients in the third Fourier series, and the fourth set of coefficients in the fourth Fourier series being selected such that a resultant third combined electrical field formed by superposition forms a local maximum at the cancerous tumor.

4. The brassiere of claim 3, wherein each of the first, second, third and fourth magnetic coils are positioned within the brassiere to approximate edges of four respective hulls that together approximate a Reuleaux tetrahedron.

5. The brassiere of claim 1, wherein the cup further comprises a plurality of seams, the seams enclosing the magnetic coils.

6. A method to administer electromagnetic therapy to treat a cancerous tumor within a breast, the method comprising:
providing a brassiere having at least one cup comprising at least a first magnetic coil and a second magnetic coil;
providing to the first magnetic coil a first time-domain signal consisting of a first series of summed sinusoidal waves from a first power supply, the first series of summed sinusoidal waves being representable as a first set of coefficients in a first Fourier series; and
providing to the second magnetic coil a second time-domain signal consisting of a second series of summed sinusoidal waves from a second power supply, the second series of summed sinusoidal waves being representable as a second set of coefficients in a second Fourier series, wherein the first magnetic coil and the second magnetic coil are oriented relative to each other so as to be nonparallel, the first set of coefficients in the first Fourier series and the second set of coefficients in second Fourier series being selected such that a resultant first combined electrical field formed by superposition forms a local maximum at the cancerous tumor.

7. The method of claim 6, further comprising:
energizing a third magnetic coil which the brassiere comprises with a third time-domain signal consisting of a third series of summed sinusoidal waves from a first power supply, the third series of summed sinusoidal waves being representable as a third set of coefficients in a third Fourier series, wherein the first magnetic coil, the second magnetic coil, and the third magnetic coil are oriented relative to each other such that each pair of magnetic coils is nonparallel one to the other, the first set of coefficients in the first Fourier series, the second set of coefficients in second Fourier series, and the third set of coefficients in the third Fourier series being selected such that a resultant second combined electrical field formed by superposition forms a local maximum at the cancerous tumor.

8. The method of claim 7, further comprising:
energizing a fourth magnetic coil which the brassiere comprises with a fourth time-domain signal consisting of a fourth series of summed sinusoidal waves from a first power supply, the fourth series of summed sinusoidal waves being representable as a fourth set of coefficients in a fourth Fourier series, wherein the first magnetic coil, the second magnetic coil, the third magnetic coil, and the fourth magnetic coil are oriented relative to each other such that each pair of magnetic coils is nonparallel one to the other, the first set of coefficients in the first Fourier series, the second set of coefficients in the second Fourier series, the third set of coefficients in the third Fourier series, and the fourth set of coefficients in the fourth Fourier series being selected such that a resultant third combined electrical field formed by superposition forms a local maximum at the cancerous tumor.

9. The method of claim 8, wherein the each of the first, second, third and fourth magnetic coils are positioned within the brassiere to approximate edges of four respective hulls that together approximate a Reuleaux tetrahedron.

10. The method of claim 6, wherein the at least one cup further comprises a plurality of seams, the seams enclosing the magnetic coils.

11. A brassiere assembly to administer electromagnetic therapy to treat a cancerous tumor within a breast, the brassiere assembly comprising:
a brassiere having a therapeutic cup, the therapeutic cup including a plurality of solenoid coils, the coils in nonparallel alignment, each to the others; and
a signal generator for independently energizing each of the plurality of solenoid coils, wherein the plurality of solenoid coils are positioned within the therapeutic cup to approximate a Reuleaux tetrahedron.

12. The brassiere assembly of claim 11 wherein the signal generator comprises:
a Fourier summing engine to generate summed signals by summing of sinusoids based upon Fourier coefficients provided to the summing engine.

13. The brassiere assembly of claim 12 wherein each of the plurality of solenoid coils receives a distinct signal based upon a distinct series of Fourier coefficients provided to the Fourier summing engine.

14. The brassiere assembly of claim 13 wherein each of the distinct series of Fourier coefficients are selected to generate a designated field at a tumor site within a volume of breast tissue the therapeutic cup encloses, summed from the influence of the plurality of solenoid coils by superposition of magnetic fields.

15. The brassiere assembly of claim 14 wherein the designated field is selected to mimic electromagnetic fields associated with a therapeutic dosage applied to the cancerous tumor with a selected anti-cancer drug.

* * * * *